(12) United States Patent
Ware et al.

(10) Patent No.: US 6,232,073 B1
(45) Date of Patent: May 15, 2001

(54) NUCLEIC ACID MARKER FOR CANCER

(75) Inventors: Joy L. Ware; Chavaboon Dechsukhum; Carleton T. Garrett, all of Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 0 days.

(21) Appl. No.: 09/434,620

(22) Filed: Nov. 5, 1999

Related U.S. Application Data

(60) Provisional application No. 60/118,749, filed on Feb. 5, 1999.

(51) Int. Cl.[7] .............................. C12Q 1/68; C12P 19/34; C07H 21/04
(52) U.S. Cl. ......................... 435/6; 435/91.2; 435/91.21; 536/23.1; 536/23.5; 536/24.31; 536/24.33
(58) Field of Search .......................... 435/6, 91.2, 91.21; 536/23.1, 23.5, 24.31, 24.33

(56) References Cited

U.S. PATENT DOCUMENTS

| | | | |
|---|---|---|---|
| 5,643,729 | 7/1997 | Taniguchi et al. | 435/6 |
| 5,670,314 | 9/1997 | Christman et al. | 435/6 |
| 5,670,317 | 9/1997 | Ladanyi et al. | 435/6 |
| 5,726,288 | 3/1998 | Call et al. | 530/350 |
| 5,807,995 | 9/1998 | Cohen et al. | 530/35 D |

OTHER PUBLICATIONS

Algar et al. Human Mutation. 5(3): 221–227, 1995.*
Dechsukhum et al. Proceedings of the American Association for Cancer Research. 39: 624, abstract #4246, 1998.*
Y. Ohshima et al., "Signals for the Selection of a Splice Site in Pre–mRNA Computer Analysis of Splice Junction Sequences and Like Sequences", *J. Mol. Biol.*, vol. 195, pp. 247–259, 1987.

K. Pritchard–Jones et al., "The Candidate Wilms' Tumour Gene is Involved in Genitourinary Development", *Nature*, vol. 346, pp. 194–197, 1990.

S. Madden et al., "A Structure–Function Analysis of Transcriptional Repression Mediated by the WT1, Wilms' Tumor Suppressor Protein", *Oncogene*, vol. 8, pp. 1713–1720, 1993.

W. Bruening et al., "A Non–AUG Translational Initiation Event Generates Novel WT1 Isoforms", *The Journal of Biological Chemistry*, vol. 271, No. 15, pp. 8646–8654, 1996.

S. Barbaux et al., "Donor Splice–site Mutations in WT1 are Responsible for Frasier Syndrome", *Nature Genetics*, vol. 17, pp. 467–470, 1997.

(List continued on next page.)

*Primary Examiner*—Carla J. Myers
(74) *Attorney, Agent, or Firm*—McGuireWoods, LLP

(57) ABSTRACT

The present invention provides using a truncated WT1 gene transcript as a marker for detecting cancer in a subject. The method provides detecting the truncated WT1 gene transcript in a sample from the subject where the truncated gene transcript is characterized by an absence of a 101 base pair segment of intron 5 between nucleic acid positions –101 and –1. Positive detection of the truncated WT1 gene transcript indicates the presence of cancer. The invention provides a truncated WT1 gene transcript characterized by an absence of a 101 base pair segment of intron 5 between nucleic acid positions –101 and –1 and having a length of about two thousand base pairs. The truncated gene transcript is further characterized by containing at their five prime end sequences normally confined to the fifth intron of the WT1 gene, exons six through ten at their three prime end, and an overall length of approximately 2 kb.

18 Claims, 11 Drawing Sheets

OTHER PUBLICATIONS

S. Plymate et al., "The Effect on the Insulin–Like Growth Factor System in Human Prostate Epithelial Cells of Immortalization and Transformation by Simiam Virus–40 T Antigen", *Journal of Clinical Endocrinology and Metabolism*, pp. 3709–3716, 1996.

G. Dong et al., "Decreased Expression of Wilms' Tumor Gene WT–1 and Elevated Expression of Insulin Growth Factor–II (IGF–II) and Type 1 IGF Receptor Genes in Prostatic Stromal Cells from Patients with Benign Prostatic Hyperplasia", *Journal of Clinical Endocrinology and Metabolism*, vol. 82, No. 7, pp. 2198–2203, 1997.

H. Werner et al., "Transcriptional Repression of the Insulin–like Growth Factor I Receptor (IGF–I–R) Gene by the Tumor Suppressor WT1 Involves Binding to Sequences Both Upstream and Downstream of the IGF–I–R Gene Transcription Start Site", *The Journal of Biological Chemistry*, vol. 269, No. 17, pp. 12577–12582, 1994.

M. Coppers et al., "The Role of WT1 in Wilms Tumorigenesis", *The FASEB Journal*, vol. 7, pp. 886–895, 1993.

J. Pelletier et al, "Expression of the Wilms' Tumor Gene WT1 in the Murine Urogenital System", *Gene & Development*, vol. 5, pp. 1345–1356, 1991.

M. Gessler et al., "The Genomic Organization and Expression of the WT1 Gene", *Genomics*, vol. 12, pp. 807–813, 1992.

M. Kaighn et al., "Establishment and Characterization of a Human Prostatic Carcinoma Cell Line (PC–3)", *Investigative Urology*, vol. 17, No. 1, pp. 16–23, 1979.

V. Bae et al., "Tumorigenicity of SV40 T Antigen Immortalized Human Prostate Epithelial Cells: Association with Decreased Epidermal Growth Factor Receptor (EGFR) Expression", *Int. J. Cancer*, pp. 721–729, 1994.

C. Walker et al., "Wilms' Tumor Suppressor Gene Expression in Rat and Human Mesothelioma", *Cancer Research*, vol. 54, pp. 3101–3106, 1994.

C. Saris et al., "The Pim–1 Oncogene Encodes Two Related Protein–Serine/Threonine Kinases by Alternative Initiation at AUG and CUG", *The EMBO Journal*, vol. 10, No. 3, pp. 655–664, 1991.

C. Englert et al., "WT1 Suppresses Synthesis of the Epidermal Growth Factor receptor and Induces Apoptosis", *The EMBO Journal*, vol. 14, No. 19, pp. 4662–4675, 1995.

R. Shimamura et al., "The Wilms' Tumor Gene WT1 Can Regulate Genes Involved in Sex Determination and Differentiation: SRY, Mullerian–inhibiting Substance, and the Androgen Receptor", *Clinical Cancer Research*, vol. 3, pp. 2571–2580, 1997.

J. Pelletier et al., "Germline Mutations in the Wilms' Tumor Suppressor Gene are Associated with Abnormal Urogenital Development in Denys–Drash Syndrome", *Cell*, vol. 67, pp. 437–447, 1991.

K. Nichols et al., "WT1 Induces Expression of Insulin–like Growth Factor 2 in Wilms' Tumor Cells", *Cancer Research*, vol. 55, pp. 4540–4543, 1995.

P. Chomczynski et al., "Single–Step Method of RNA Isolation by Acid Guanidinium Thiocyanate–Phenol–Chloroform Extraction", *Analytical Biochemistry*, vol. 162, pp. 156–159, 1987.

L. King–Underwood et al., "Mutations in the Wilms' Tumor Gene WT1 in Leukemias", *Blood*, vol. 87, pp. 2172–2179, 1996.

C. Jackson–Cook et al., "Cytogenetic Characterization of the Human Prostate Cancer Cell Line P69SV40T and its Novel Tumorigenic Sublines M2182 and M15", *Cancer Genet Cytogenet*, vol. 87, pp. 14–23, 1996.

M. Emmert–Buck et al., "Laser Capture Microdissection", *Science*, vol. 274, pp. 998–1001, 1996.

A. Schedl et al., "Multiple Roles for the Wilms' Tumor Suppressor Gene, WT1 in Genitourinary Development", *Moleculr and Cellular Endocrinology*, vol. 140, pp. 65–69, 1998.

H. Werner et al., "The Regulation of IGF–I Receptor Gene Expression by Positive and Negative Zinc–Finger Transcription Factors", *Adv. Exp. Med. Biol.*, vol. 343, pp. 91–103, 1994.

S. Park et al., "The Wilms Turmour Gene WT1 is Expressed in Murine Mesoderm–derived Tissues and Mutated in a Human Mesothelioma", *Nature Genetics*, vol. 4, pp. 415–420, 1993.

I. Drummond et al., "Repression of the Insulin–Like Growth Factor II Gene by the Wilms Tumor Suppressor WT1", *Science*, vol. 257, pp. 674–678, 1992.

Z. Wang et al, "A Second Transcriptionally Active DNA–binding Site for the Wilms Tumor Gene Product, WT1", *Proc. Natl. Acad. Sci. USA*, vol. 90, pp. 8896–8900, 1993.

H. Prats et al., "High Molecular Mass Forms of Basic Fibroblast Growth Factor are Iniated by Alternative CUG Codons" *Proc. Natl. Acad. Sci. USA*, vol. 86, pp. 1836–1840, 1989.

V. Bae et al., "Metastatic Sublines of an SV40 Large T Antigen Immortalized Human Prostate Epithelial Cell Line", *The Prostate*, vol. 34, pp. 275–282, 1998.

M. Edmonds, "Polyadenylic Acid Sequences in the Heterogeneous Nuclear RNA and Rapidly–Labeled Polyribosomal RNA of HeLa Cells: Possible Evidence for a Precursor Relationship", *Proc. Natl. Acad. Sci. USA*, vol. 68, No. 6, pp. 1336–1340, 1971.

* cited by examiner

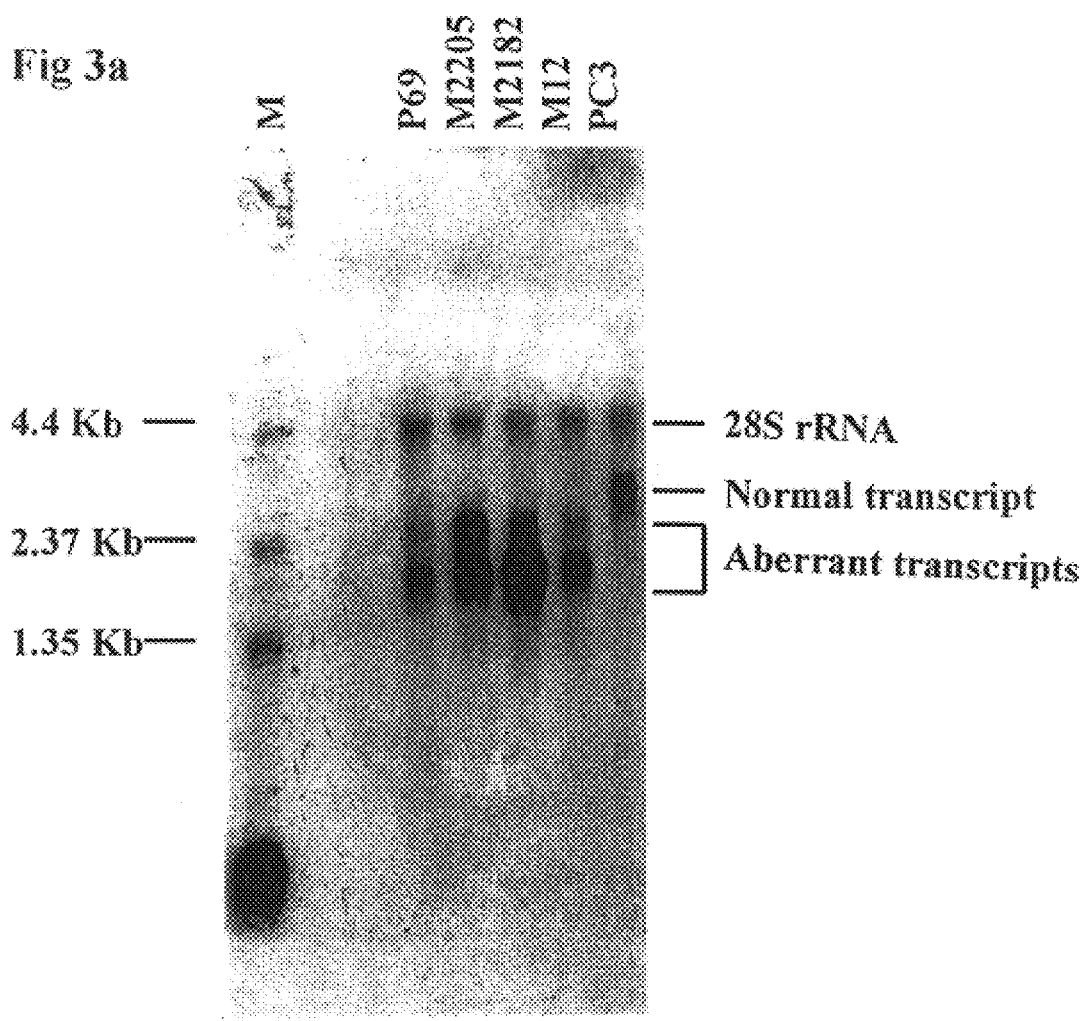

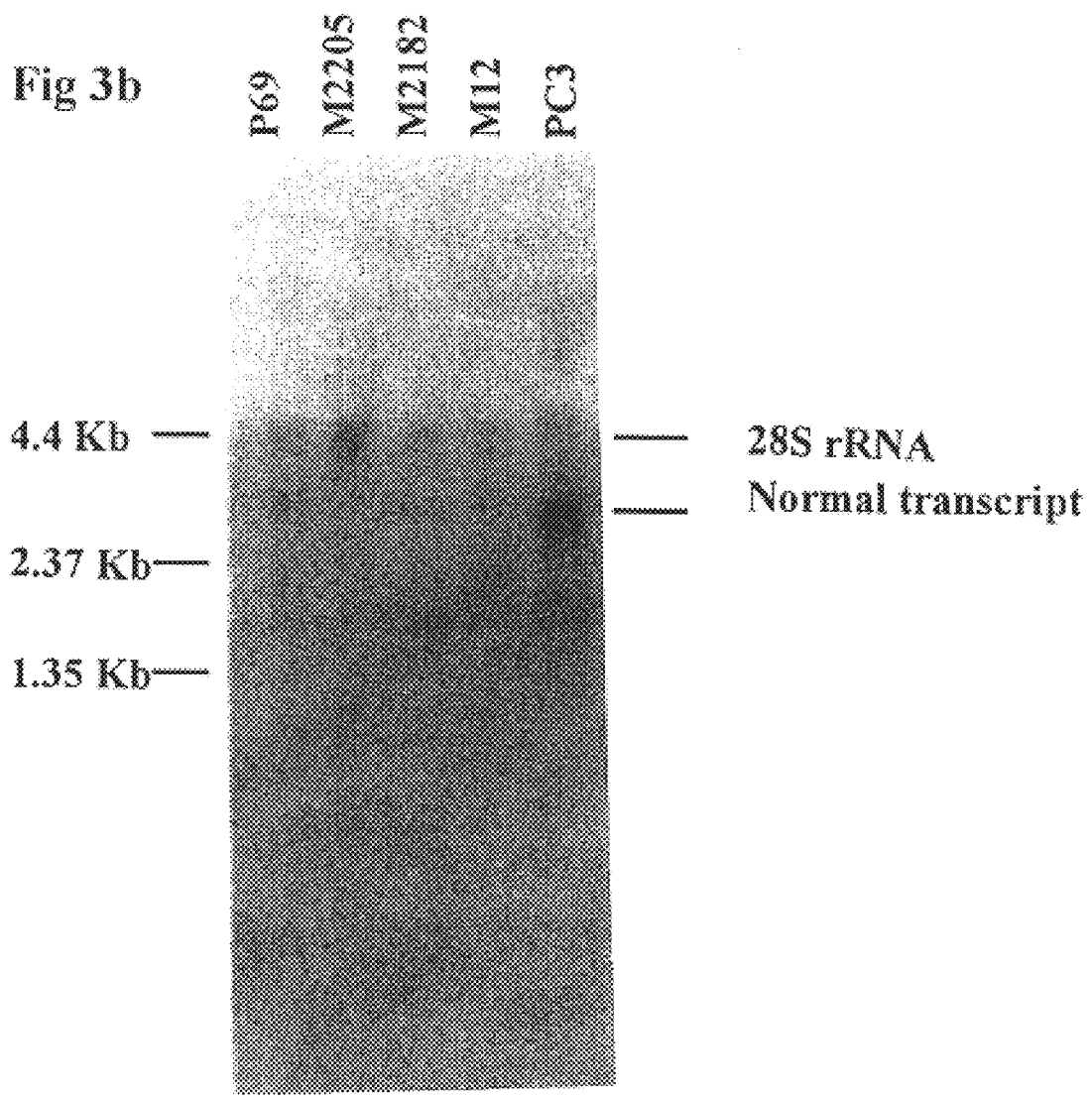

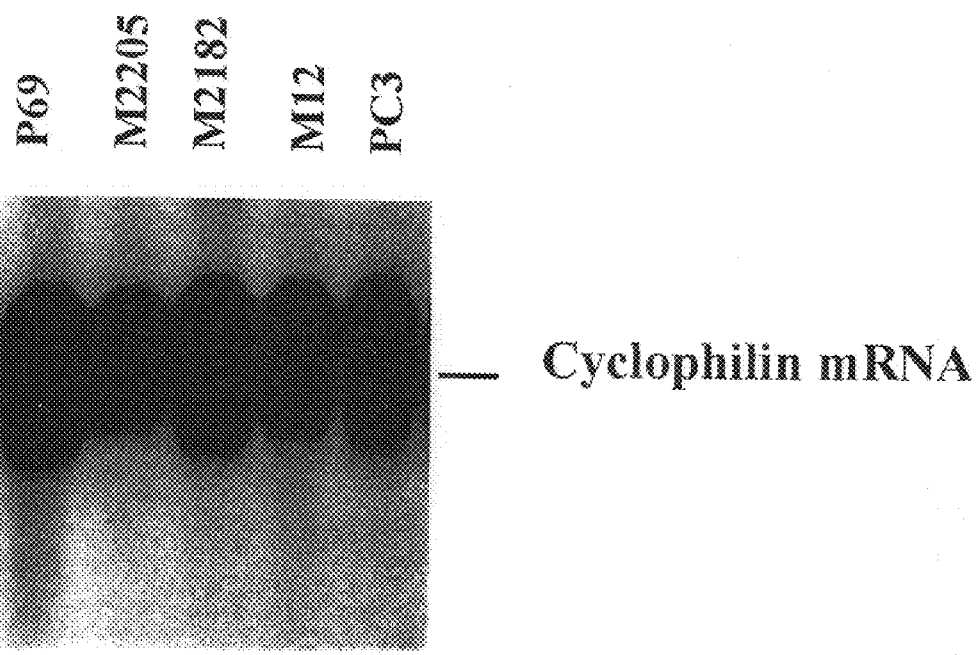

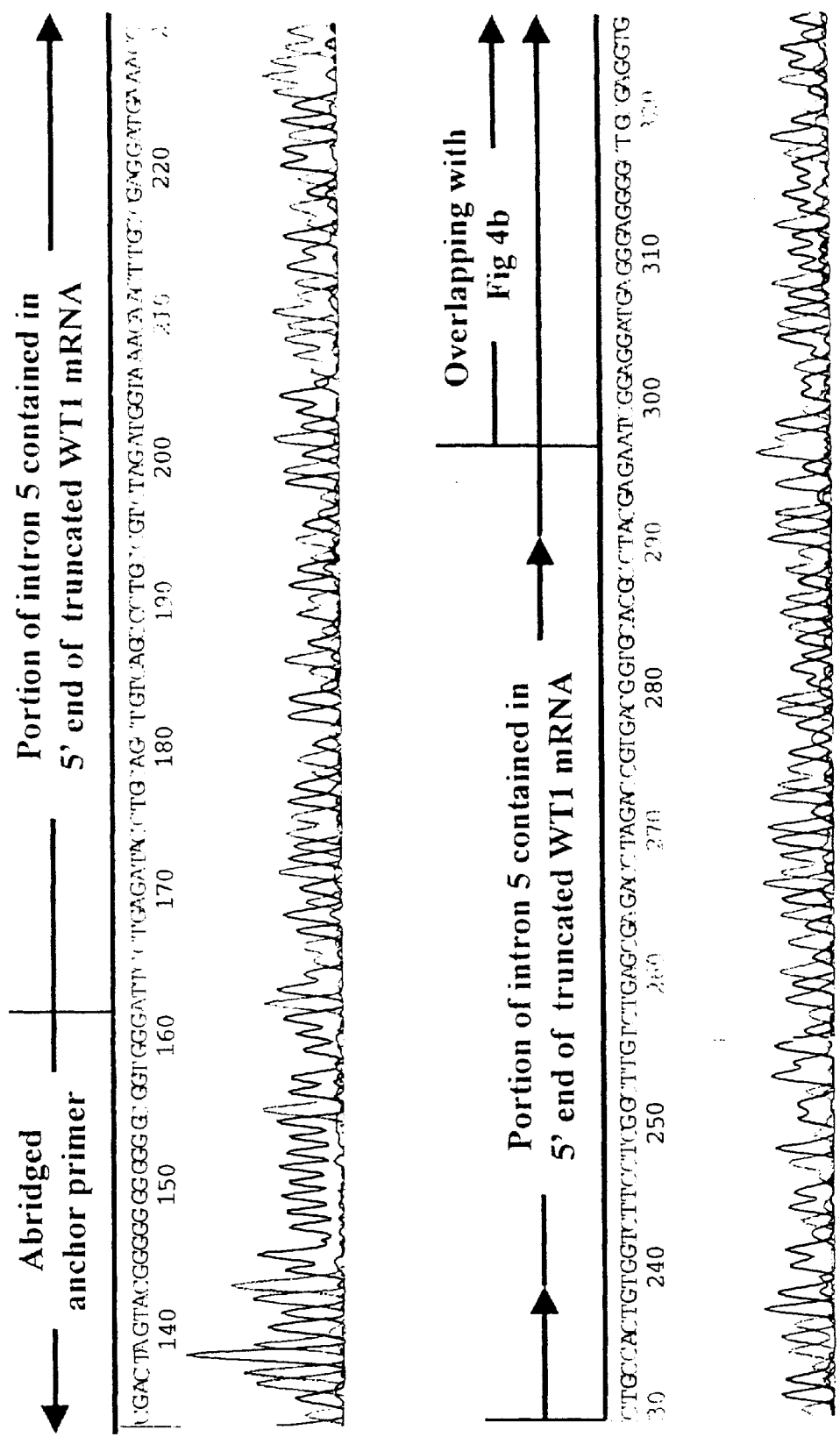

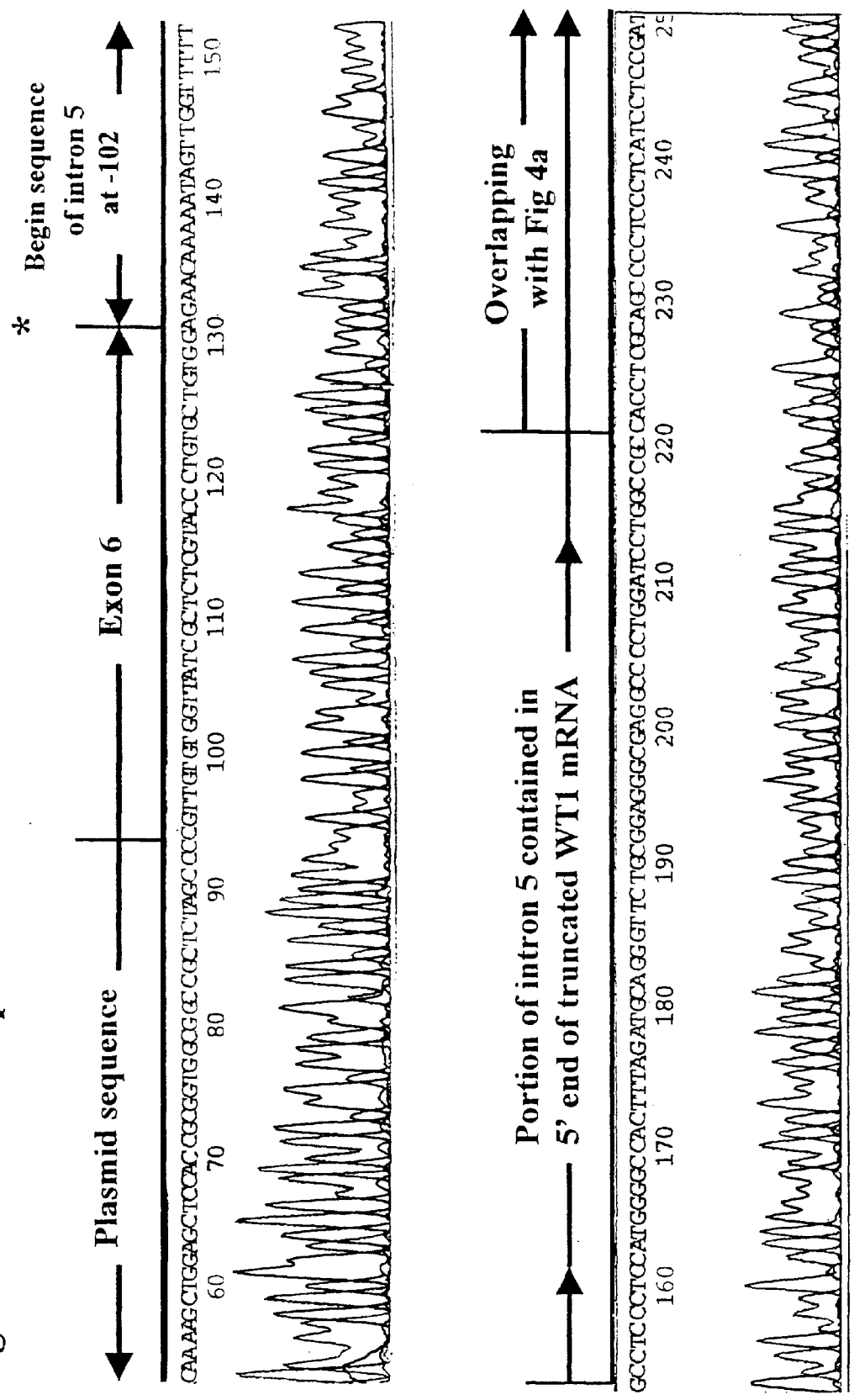
Fig 4b 3'-5' trancript

Fig. 4c Truncated WT1 5'-3'

ATTCCTGAGA TACCTGCAGC TGTCAGCCCT GCCGTCTAGA TGGTAAACAA
CTTGCCGAGG ATGAAACCCT GCCACTGTGG TCTTCCTCGG CTTGTCTGAG
CGAGACCTAG ACCGTGACGG TGCACGCCTA CGAGAATCGG AGGATGAGGG
AGGGGCTGCG AGGTGGGCGGC CAGGATCCAG GGGCCTCGCC CTCCGCAGAA
CCCTGCATCT AAAGTGGCCC CATGGAGGGA GGCAAAAACC AACTATTTT GTTCT

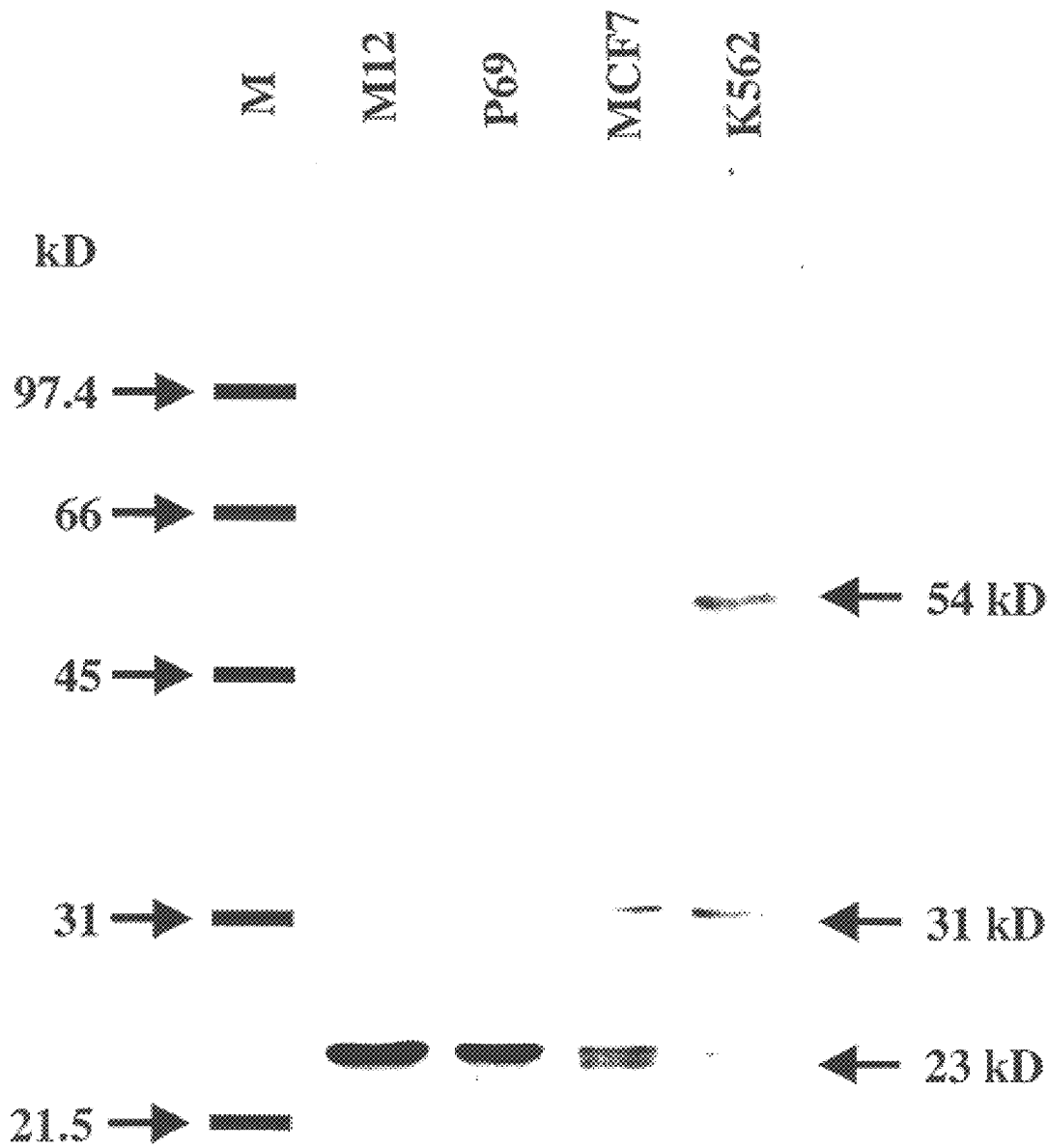

NUCLEIC ACID MARKER FOR CANCER

This Application claims the benefit of U.S. Provisional Application No. 60/118,749, filed Feb. 5, 1999, herein incorporated by reference in its entirety.

The invention was made with Government support under DAMD17-98-1-8540 awarded by U.S. Army Medical Research Acquisition Activity. The Government has certain rights in the invention.

BACKGROUND OF THE INVENTION

The present invention relates broadly to a method for identifying cancer or neoplastic tissue in a subject.

The Wilms' Tumor 1 (WT1) gene encodes a transcription factor that is critical to normal urogenital development. However, the role of WT1 in prostatic disease is not known. Decreased expression of WT1 and increased expression IGF-1 receptors have been reported in stromal cells from benign hyperplastic prostate tissue, as compared with stromal cells from normal or malignant prostate. WT1 has been shown to regulate the transcription of several growth factors and growth factor receptors that are implicated in prostatic growth control, specifically, the epidermal growth factor receptor (EGFR), insulin-like growth factor (IGF II), the IGF type I receptor (IGFR I), and the androgen receptor.

The WT1 gene product may activate or repress target gene transcription, depending on which of the four isoforms is produced by the cell. The impact of WT1 on target gene transcription is also influenced by cell type and the presence or absence of other proteins that interact with WT1, such as p53, the prostatic apoptosis response protein PAR-4 known as PAWR and CIOA 1 which have been shown to decrease the transcriptional activation of WT1.

SUMMARY OF THE INVENTION

Earlier studies led to the development of a model of human prostate cancer progression that permits comparison of the cellular properties and molecular properties of increasingly aggressive sublines of SV40 large T-antigen immortalized human prostate epithelial cells within the same lineage. These cell lines display the following phenotypes, assessed by orthotopic and/or subcutaneous injection into athymic nude mice: immortal, nontumorigenic; tumorigenic but nonmetastatic, and consistently tumorigenic and metastatic. The expression of EGFR decreased dramatically in metastatic M12 cells, as compared with the parental line. Additional investigations were conducted to determine whether WT1 was expressed in any of the sublines and whether expression correlated with the alteration in the in vivo phenotype and/or the reduction in EGFR and IGFR. These investigations led to the unexpected finding of a truncated WT1 gene transcript with implications for the role of WT1 oncogenesis.

Accordingly, it is an object of the invention to provide a method for detecting cancer or neoplastic tissue in a subject. Further, it is an object of the present invention to provide a method for identifying cancer or neoplastic tissue in a subject by identifying the presence of a truncated Wilms' Tumor 1 (WT1) gene transcript. Further, the present invention is directed to a truncated WT1 gene transcript and a method of using the truncated WT1 gene transcript as a tumor marker for various forms of cancer that express the WT1 gene transcript.

The present invention provides a method for detecting cancer in a subject. The method provides obtaining a sample from the subject and detecting a truncated WT1 gene transcript in the sample, wherein the presence of the truncated WT1 gene transcript indicates the presence of cancer. Further the invention provides detecting a truncated WT1 gene transcript that includes a portion of intron 5. The invention further provides a truncated WT1 gene transcript that lacks a 101 base pair segment of intron 5 between −101 and −1. Still further, the invention includes a truncated WT1 gene transcript characterized by the sequence shown in FIG. 4.

Further, the invention provides a method where the detection of the truncated WT1 gene transcript includes performing reverse transcriptase-polymerase chain reaction using a 5 prime primer located in intron 5 and a 3 prime primer located in exon 6. Still further, the invention provides using a primer for reverse transcriptase-polymerase chain reaction where the primer is 5'-GAA CCC TGC ATC TAA AGT GG-3' (SEQ ID NO: 1).

The invention also provides detecting the truncated WT1 gene transcript by probing products from the reverse transcriptase-polymerase chain reaction with an oligonucleotide sense primer in exon 6 wherein the oligonucleotide sense primer is 5'-CCA CAG CAAC AGG GTA CGA-3' (SEQ ID NO: 2). Further, the invention provides identifying a 95 base pair fragment representing a product of the truncated WT1 gene transcript.

Still further, the invention provides detecting a truncated gene transcript having a length of about two thousand base pairs.

The invention provides a method where positive detection indicates the presence of prostate cancer. The invention also provides a method where positive detection indicates the presence of breast cancer. The invention further provides a method where positive detection indicates the presence of leukemia.

Still further, the invention provides a method for detecting a truncated WT1 gene transcript that includes obtaining a nucleic acid sample from a subject suitable for performing reverse transcriptase-polymerase chain reaction. The method also provides performing reverse transcriptase-polymerase chain reaction on the nucleic acid sample using a 5 prime primer located in intron 5 and a 3 prime primer located in exon 6. The method further provides probing products from the reverse transcriptase-polymerase chain reaction with an oligonucleotide sense primer in exon 6. The method provides identifying a fragment representing a product of the truncated WT1 gene transcript. The invention provides probing products from the reverse transcriptase-polymerase chain reaction with an oligonucleotide sense primer in exon 6, wherein the oligonucleotide sense primer is 5'-CCA CAG CAC AGG GTA CGA-3' (SEQ ID NO: 2). The invention also provides for performing reverse transcriptase-polymerase chain reaction with a primer, wherein the primer is 5' GAA CCC TGC ATC TAA AGT GG-3' (SEQ ID NO: 1). The invention further provides identifying a 95 base pair fragment.

Further, the invention provides an isolated nucleic acid that includes a truncated WT1 gene transcript characterized by the inclusion of a portion of intron 5. The invention further provides an isolated nucleic acid characterized by an absence of a 101 base pair segment of intron 5 between −101 and −1 and has a length of about two thousand base pairs. Still further, the invention provides an isolated nucleic acid characterized by the sequence shown in FIG. 4.

BRIEF DESCRIPTION OF THE DRAWINGS

FIGS. 3a–c are a Northern blot analyses of expression of expected 3.1 kb WT1 mRNA, novel WT1 mRNA (2 kb), and cyclophilin mRNA (loading control). FIG. 3a is a Northern blot hybridized with probe spanning 3' end of WT1 (exon 7–10) (Table 1). FIG. 3b is a Northern blot hybridized with probe spanning 5' end of WT1 (exon 1–5) (Table 1). Sample loading was normalized by comparison with stripped blot re-probed with riboprobe complementary to cyclophilin mRNA and is shown in FIG. 3c.

FIGS. 4a–c show the PCR product obtained from the 5' RACE procedure performed on mRNA from M12 cell was cloned and sequenced.

FIG. 5 shows the expression of WT1 protein detected by western immunoblotting in human prostate cancer cell lines P69 and M12; breast cancer cell line, MCF7; and, leukemia cell line, K562.

DESCRIPTION OF THE PREFERRED EMBODIMENTS

The present invention is directed to a novel truncated WT1 gene transcript and its use as a tumor marker for cancer. Using reverse transcriptase-polymerase chain reaction (RT-PCR), northern blotting analysis, and 5'-RACE, the WT1 transcripts contain at their five prime end sequences normally confined to the fifth intron of the WT1 gene. Further, the WT1 transcripts contain exons six through ten at their three prime end and an overall length of approximately 2 kb.

Although mutations of WT1 have been described in Wilms' tumors, mesotheliomas, leukemias, the Denys-Drash syndrome and the Frasier syndrome, most of these involve insertions or point mutations in exon 1, 7 or 9 with loss of all or part of the zinc finger region. Splice-donor site mutations in intron 9 have been reported in cases of Frasier syndrome.

Figure 7:
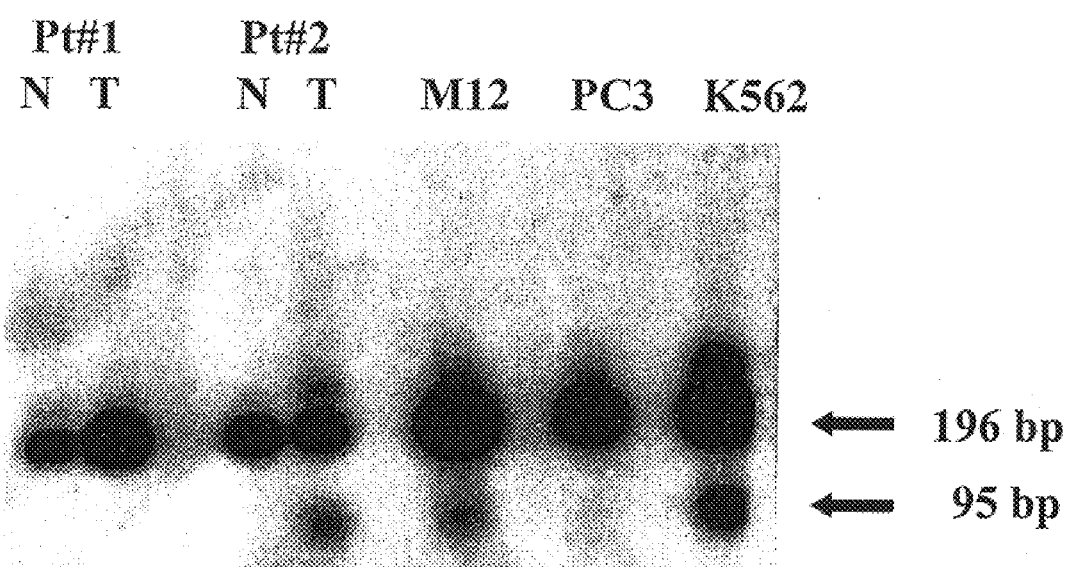
FIG. 7 shows the RT-PCR product using primers in intron 5 and exon 6. Total RNA was obtained from microdissected frozen normal (N) and primary prostate cancer (T) tissue from two patients and from M12, PC3 and K562 lines.

The production of this novel, short transcript occurs in both human prostate cell lines generated by immortalization with the SV40 large T antigen gene and the human breast cancer cell line MCF7, which was derived originally from a spontaneous breast cancer. Utilizing primers in intron 5 and exon 6, this novel transcript was detected in microdissected prostate tumor cells, but not in normal or benign hyperplastic prostate epithelium cells from the same patient (FIG. 7). This shows the ability of this mutation to be used as a tumor marker. These novel transcripts were also found in blood samples from acute leukemia and breast cancer by RT-PCR, but not in normal peripheral blood lymphocytes further showing its use as a tumor marker.

The possibility that the transcript specific signals resulted from DNA contamination was eliminated by virtue of the fact that the primers spanned the portion of the transcript exhibiting the 101 bp deletion from nucleotides −101 to −1 and consequently produced a PCR product that was shorter than that generated by DNA. Thus expression of 2 kb WT1 transcripts similar to that shown in FIG. 4 was observed in spontaneous human cancers as well as cancer cell lines.

The mechanism(s) by which this 2 kb WT1 transcript might contributer to tumor cell aggressiveness is unclear at this time. However, as shown in FIG. 4, sequence analysis reveals the absence of most of the transactivation region of WT1. It is believed that the remaining sequence of the truncated WT1 transcript remains substantially the same as the normal WT1 transcript or contains only minor deviations. Without intending to be bound by theory, it is believed that the lack of the transactivation domain is likely to alter the functional consequences of increased production of this WT1 gene product. Given the effect of interaction with other proteins on the biological consequence of WT1 expression (P53, PAR- 4, CIAO 1, and Hsp 40), the protein encoded by this short transcript may contribute directly and/or indirectly to the tumorigenic and/or metastatic capacity of M12 cells.

EXAMPLE 1

The Truncated Wilms' Tumor Gene Transcript
Human tumor cell lines.

Prostate cell lines were routinely maintained serum-free in RPMI 1640 supplemented with dexamethosone (0.1 $\mu$M), insulin, transferring and selenious acid (ITS; insulin, 5 $\mu$g/ml, transferring, 5 $\mu$g/ml, and selinium, 5 ng/ml), epidermal growth factor (EGF) (10 ng/ml) (Collaborative Research, Bedford, Mass.) and gentamicin (0.05 $\mu$g/ml) (Gibco/BRL, Rockville, Md.). The parental P69SV40T cell line and the derivation of its tumorigenic and metastatic sublines were described in detail previously (Bae, V. L. et al., *Int. J. Cancerl*, 58, 721–729 (1994) herein incorporated by reference; Jackson-Cook, C. et al., *Cancer Genet. Cytogenet*, 87, 14–23 (1996) herein incorporated by reference; Bae, V. L. et al., *Prostate*, 34, 275–282 (1998)) herein incorporated by reference. Briefly, adult human non-neoplastic prostate epithelial cells were isolated from the prostate of a 63 year old African-American man undergoing transurethral resection and cells were immortalized by transfection with the SV40 T antigen gene previously (Bae, V. L. et al., *Int. J. Cancerl*, 58, 721–729 (1994)) herein incorporated by reference. Rare tumors arising in 2/18 athymic nude mice were recovered and subjected to sequential in vitro and in vivo growth cycles, to permit isolation of increasingly aggressive sublines (Jackson-Cook, C. et al., *Cancer Genet. Cytogenet*, 87, 14–23 (1996); Bae, V. L. et al., *Prostate*, 34, 275–282 (1998)).

The PC-3 human prostate carcinoma cell line was originally isolated from a prostate cancer bone metastasis (Kaighn, M. E. et al., *Invest. Urol.*, 17, 16–23 (1979) herein incorporated by reference; PC-3 cells used in this study were obtained from a PC-3 stock and maintained in 10% fetal bovine serum (HyClone Laboratory Inc., Logan, Utah)). The K562 and MCF7 cell lines were purchased from the American Type Cell Culture (ATCC, Rockville, Md.). The K562 cells were cultured in RPMI 1640 supplemented with 15% fetal bovine serum. MCF7 was grown in minimum essential medium eagle (MOD) supplemented with insulin, transferrin and selenious acid (ITS; insulin, 5 $\mu$g/ml, transferrin, 5 $\mu$g/ml, and selinium, 5 ng/ml), 10% fetal bovine serum and gentamicin (0.05 $\mu$g/ml).

All cells were Mycoplasma—free, as assessed by the Gen-Probe Mycoplasma T. C. Rapid Detection system (Gen-Probe, San Diego, Calif.).

RNA Extraction

Total RNA was extracted from freshly isolated cultured cells using phenol/isothiocyanate procedure (Ultraspec reagent and extraction protocol; Biotex Laboratory, Inc., Houston, Tex.; Chomczynski, P. et al., *Anal. Biochem.*, 162, 156–159 (1987) herein incorporated by reference). The total RNA was dissolved in diethyl pyrocabonate treated double distilled water (DEPC-treated water) and Rnase inhibitor (Rnasin 1U/μl), (Promega, Madison, Wis. (Blackburn, P. et al., *J. Biol. Chem.* 252, 5904–5910 (1977) herein incorporated by reference; Blackburn P. et al., *J. Biol. Chem.*, 257, 316–321 (1982) herein incorporated by reference) and stored at −80° C. until use. Messenger RNA was prepared from total RNA by oligo (dT) column purification (Five Prime→Three Prime, Inc., Boulder, Colo.). A total of 1 μg of RNA was applied to the column and the mRNA fraction was eluted with elution buffer (10 mM Tris-HCl, 1 mM EDTA, pH 7.5) according to the manufacturer's protocol (Edmonds, M. et al., *Proc. Natl. Acad. Sci. USA.*, 68, 1336–1340 (1971) herein incorporated by reference). The resulting mRNA was stored in DEPC-treated water in the presence of Rnasin at −80° C. until use.

RT-PCR

Total RNA (0.7 μg) was used in an RT-PCR. The RT step was performed at 42° C. in 75 mM KCl, 50 mM Tris (pH 8.3), 3.0 mM MgCl2 (Gibco/BRL), 500 mM dNTPs (Promega), 2 μM primers and 4.2 U/μl Moloney Murine Leukemia Virus (M-MLV) reverse transcriptase (Gibco/BRL) for 1 hour followed by MMLV heat inactivation at 95° C. for 5 mins. The cDNA was then transferred to a PCR master mix with a resulting concentration of 56 mM KCl, 19.6 mM Tris (pH 8.3), 1.6 mM $MgCl_2$ (Gibco/BRL), 200 μM dNTPs (Promega) and 1 μM of primers. Forty cycles of PCR were performed using 95° C. denaturing temperature for 1 min, 60° C. annealing temperature for 30 secs, and 72° C. extension temperature for 1 min (GeneAmp PCR system 9600 Thermal Cycler (Perkin Elmer, Foster City, Calif.). The primer and probe sequences are shown in Table 1. The PCR products were analyzed by electrophoresis through 1.5% agarose gel at 100 V for 3 hours, then transferred to Zeta Probe membrane (Bio-Rad Laboratory, Hercules, Calif.), crossed linked by UV light (Stratagene UV cross linker (Stratagene, La Jolla, Calif.)). Filters were hybridized with oligonucleotide probes end labeled with $^{32}P$ γ-dATP (6,000 Ci/mmol) (NEN Life Science Product, Inc., Boston, Mass.) at 50–60° C. annealing temperature for 6–12 hours. Autoradiographs were performed for 24–72 hours.

Northern Blot Analysis

Northern blotting was used to determine the size of mRNA. Four micrograms of mRNA were loaded onto an 0.8% formaldehyde agarose gel and electrophoresed at 120 volts for 4 hours in formaldehyde gel-running buffer, 0.2M MOPS (pH 7.0), 8 mM sodium acetate, 1 mM EDTA (pH 8.0) (Sigma, St. Louis, Mo.). After electrophoresis, the gels were rinsed in DEPC-treated water for 10 minutes, followed by washing in 20x SSC (1x SSC is 0.15M NaCl, 0.015M sodium citrate) for 1 hour (3×20 minutes). The samples were transferred overnight to nylon membrane, crossed-linked by UV light, and subjected to hybridization for 12–20 hours (73–80° C. annealing temperature). Filters were hybridized with RNA probes constructed from the five prime and three prime ends of WT1 as described in the following paragraph. Washing was performed using low stringency buffer consisting of 1x SSC, 0.1% SDS and high stringency buffer consisting of 0.2x SSC, 0.1% SDS at 73°80° C. Autoradiography was performed for 3–5 days.

The $^{32}P$ α-rUTP (3,000 Ci/mol) labeled RNA probes were generated by in vitro transcription using MAXI script T7/T3 or Strip-EZ kit (Ambion, Inc., Woodward, Tex.). The templates were linearized plasmid (pCR-Script Amp SK (+), Stratagene) containing cloned double stranded RT-PCR fragment spanning nucleotide 579 (exon 1) to nucleotide 1159 (exon 5) for the 5' probe or RT-PCR fragment spanning nucleotide 1388 (exon 7) to nucleotide 1801 (exon 10) for the 3' probe. The template sequences were confirmed as wild type by automated DNA sequencer, ABI 373 (Perkin-Elmer).

5' RACE Procedure

To map the 5' region of the truncated WT1 transcript, the 5' rapid amplification of cDNA end (5'RACE) procedure supplied by Gibco/BRL was used. Briefly, 0.5 μg of total RNA or 0.05–0.1 μg of mRNA were used to synthesize cDNA using an RT antisense primer located in exon 8 (5'-ACC TTC GTT CAC AGT CCT TG-3' (SEQ ID NO: 3). The cDNA was then subjected to a tailing reaction by TdT (terminal deoxynucleotidyl transferase) for 10 minutes in the presence of 200 μM dCTP. The dCTP-tailed cDNA was then amplified in the first round of a heminested PCR procedure using an inner antisense primer located in exon 7 (5'-CTG CTG TGC ATC TGT AAG TGG GAC AGC-3' (SEQ ID NO: 4) and the 5' RACE Abridged Anchor Primer. PCR reactions were performed for 35 cycles using 95° C. denaturing temperature for 1 minute, 55° C. annealing temperature for 1 minute and 72° C. for 2 mins in the presence of 50 mM KCl, 20 mM Tris-HCl (pH 8.4), 1.5 mM $MgCl_2$, 100 μM dNTPs and 400 nM primers. The PCR product was then purified using a centricon-50 column (Millipore Corp., Inc., Bedford, Mass.), transferring the whole PCR reaction (50 μl) to the spin columns to which 2 ml of HPLC purified water (Fisher Scientific Co., Pittsburgh, Pa.) had previously been added. Centrifiguation was performed at 1000×g for 35 mins. The second round of nested PCR was performed on diluted purified PCR product (100 fold in HPLC water) using a 3' WT1 specific antisense primer located in exon 6 (5'-CGT TGT GTG GTT ATC GCT CT-3' (SEQ ID NO: 5) and a 5' Abridged Universal Amplification Primer under the same conditions. The PCR product was then visualized under UV light on an ethidium bromide stained 1.5% agarose gel. Southern blot was performed and the filter was hybridized with a probe in exon 6 (5'-CCA CAG CAC AGG GTA CGA-3' (SEQ ID NO: 2)) to verify the WT1 origin of the product. Finally, the PCR product was cloned using the pCR script Amp SK (+) Cloning kit (Stratagene). After screening of bacterial colonies using PCR (sense primer intron 5: 5'-GAA CCC TGC ATC TAA AGT GG-3' (SEQ ID NO: 1) and antisense primer in exon 6: 5'-CTC GTA CCC TGT GCT GTG G-3' (SEQ ID NO: 6)), the positive clones were grown in 2YT broth and the plasmid DNA was extracted by using a modified alkaline lysis procedure (PERFECT prep kit (5 Prime→3 Prime, Inc.)). Cycle sequencing was performed using flourescent dye labeled M13 forward/reverse primer kits (Perkin Elmer, Foster City, Calif.). The sequencing product was examined on an automated DNA sequencer (ABI 373); (Perking Elmer). Cycle sequencing using dye terminators (Perkin Elmer) and manual sequencing using AmpliCycle Sequencing Kit (Perkin Elmer) were also performed to confirm automated sequencer data.

Western Immunoblotting

The cells were grown to 100% confluence and protein was extracted as described elsewhere (Bae, V. L. et al., *Int. J. Cancerl*, 58, 721–729 (1994) herein incorporated by reference). Cells were washed with cold phosphate buffered saline (PBS) 3 times, incubated with protein extraction buffer (50 mM Tris pH 8.0, 0.01% NP-4, 0.001% SDS supplemented with proteinase inhibitor (Complete Proteinase Inhibitor Cocktail Tablets, (Boehringer Mannheim, Indianapolis, Ind.)) for 30 mins, scraped and transferred to 1.5-ml tubes. Samples were centrifuged at 10,000×g for 20 mins at 4° C. The supernatants were divided into 100 µl aliquots and stored at 80° C. for less than 24 hrs before loading onto a 10% SDS-polyacrylamide gel (PAGE). The samples were mixed with the same volume of 2X reducing buffer (12.14 mM Tris-HCl, 4.6% (w/v) SDS, 2.0% (v/v) β-Mercaptoethanol and 20% (v/v) glycerol) and boiled for 5 mins and quenched on ice until loading. Low range molecular weight markers (Bio-Rad Laboratory, Hercules, Calif.) were used to determine relative migration. Electrophoresis was performed at 90 mA for 3 hrs. The gels were then soaked in protein semidry transfer buffer (48 mM Tris, 39 mM glycine, 0.0375% (w/v) SDS and 20% (v/v) methanol) for 20 mins and subjected to semi-dry electrotransfer using Trans-Blot SD Semi-Dry Transfer Cell (Bio-Rad Laboratories) onto the PVDF membrane (Immobilon): (Amersham Phamacia Biotech, Arlington Heights, Ill.) at 300 mA for 3 hrs. Standards were separated and stained with Amido Black for 10 mins and washed with a 45% methanol, 10% acetic acid solution. The rest of the membranes were washed with Tris buffer saline-Tween (TTBS); (20 mM Tris-HCl, 136 mM NaCl, pH 7.6 and 0.05% (v/v) Tween 20) 3X 5 mins. Nonspecific binding was blocked with 5% milk in TTBS followed by an 1 hr incubation with 0.25 µg/ml of anti-WT1 primary antibody (C19 polyclonal antibody (Santa Cruz Biotechnology, Santa Cruz, Calif.)). Membranes were washed and subjected to secondary antibody incubation at 1:2000 dilution. After the TTBS wash, the signals were detected by enhanced chemiluminescence using the ECL+Plus detection kit (Amersham Phamacia Biotech). Signals were usually detected within 1 minute of exposure to Hyperfilm ECL (Amersham). As a specificity control, duplicate western blots were incubated in parallel with anti-WT1 antibody preincubated with the immunizing peptide supplied by the manufacturer. (Santa Cruz Biotechnology).

Figure 1:
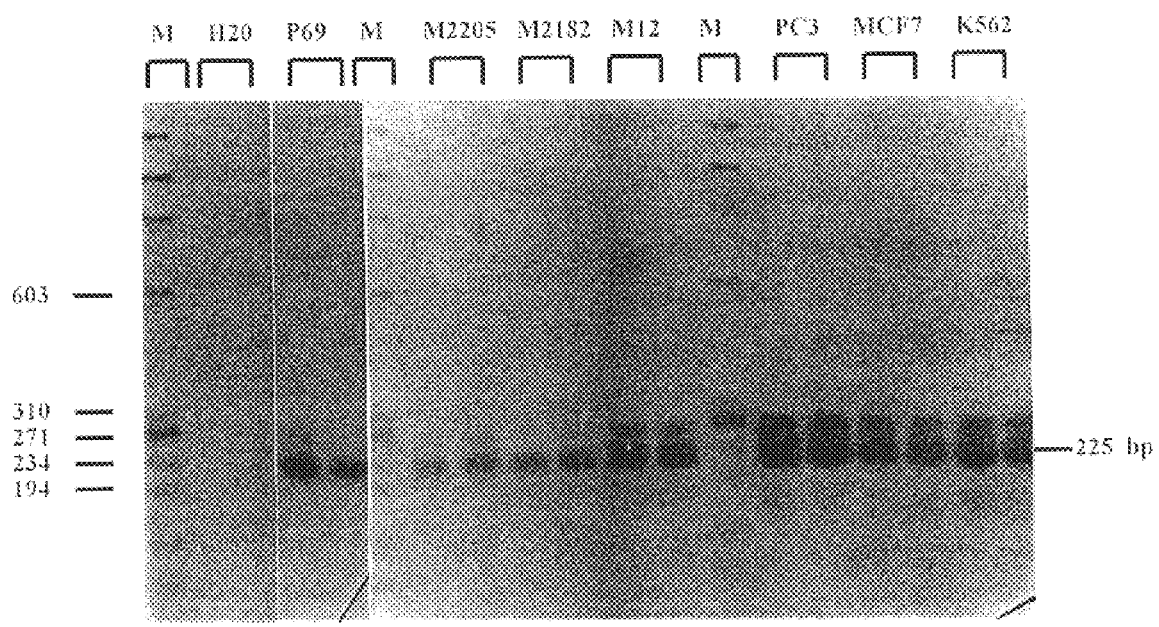
FIG. 1 is a comparison of WT1 transcripts identified in P69SV40TAg and its sublines, PC-3, MCF7 and K562 by RT-PCR across exons 8–10, using primers described in Table 1.

Using RT-PCR to amplify regions of exons 8–10 WT1, the expression of the expected 225 bp product from RNA in PC-3 cells, the parental P69SV40T cell line, the tumorigenic sublines derived from P69SV40T, as well as MCF7 and K562 control cell lines was detected as shown in FIG. 1.

FIG. 1 is a comparison of WT1 transcripts identified in P69SV40TAg and its sublines, PC-3, MCF7 and K562 by RT-PCR across exons 8–10, using primers described in Table 1. Thirty microliters of reaction product in a total volume of 100 µl were loaded per lane. The products were transferred and hybridized with a probe complimentary to exon 10 (Table 1). All cell lines including P69SV40TAg and its sublines produced the expected PCR product of 225 bp. The experiments were performed a minimum of 3 times. The lanes are identified as follows: M=>markers; H$_2$O= >negative control, water only; cell lines (source of RNA) indicated at top of figure. RNA sample from each line run in duplicate as indicated by brackets.

Figure 2:
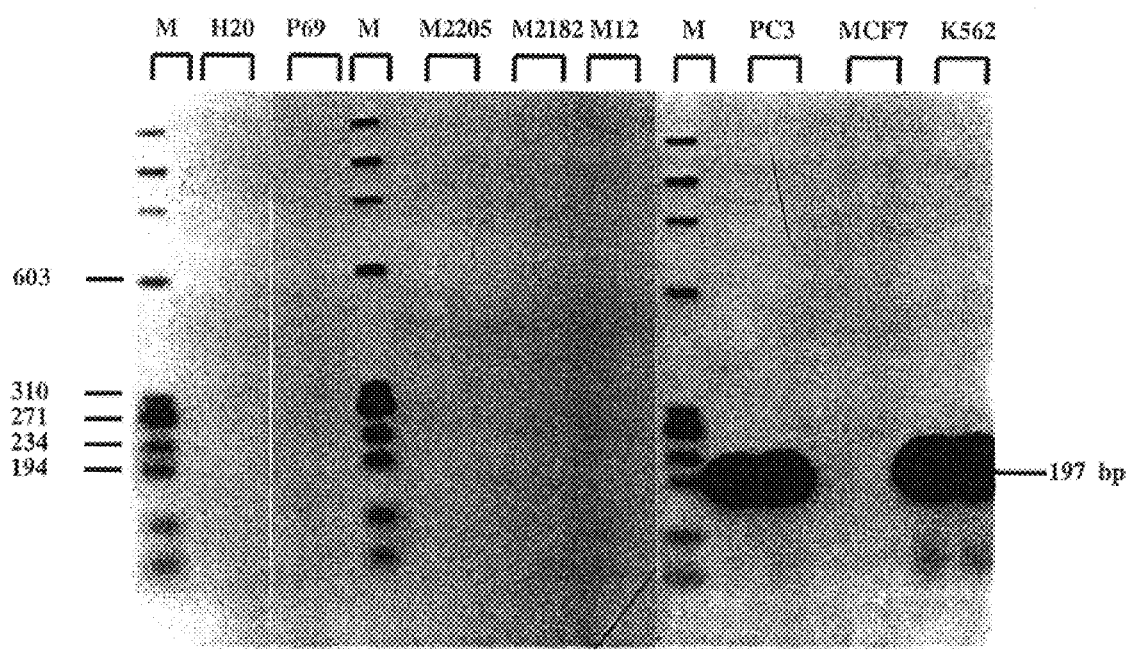
FIG. 2 is a comparison of WT1 transcripts identified by RT-PCR across exons 1–2 of WT1, using primers described in the Table 1, for PC-3 cells, the P69SV40TAg sublines and MCF7.

The origin of the product from WT1 was confirmed through the hybridization of each of the products with a probe located in exon 10 (Table 1). In contrast, RT-PCR was performed using primers that spanned the first splice junction (exon 1–exon 2), no products were detected in P69SV40TAg or any of its sublines as shown in FIG 2. Furthermore, no products were detected in MCF7 cells. As shown in FIG. 2, the expected fragment was present in PC-3 cells and in K562 cells.

FIG. 2 is a comparison of WT1 transcripts identified by RT-PCT across exons 1–2 of WT1, using primers described in Table 1, for PC-3 cells, the P69SV40TAg sublines and MCF7. After RT-PCR, the products were transferred and hybridized with a probe complimentary to the 3' end of exon 1 (Table 1). Note the presence of WT1 transcript in PC-3 and positive control K562 but its absence in P69SV40 TAg and its sublines. No signal was detected from MCF7 as well. The experiments were performed a minimum of 3 times. The lanes are identified as follows: M=>markers; H$_2$O= >negative control, water only; cell lines (source of RNA) indicated at top. An RNA sample from each line run is in duplicate and indicated by brackets.

Next, RNA was examined using primer pairs that spanned each of the splice junctions for introns 2–6. No product was detected for any of the P69 family except for primers across the $6^{th}$ splice junction (exon 6–exon 7).

FIG. 3 is a northern blot analysis of expression of expected 3.1 kb WT1 and mRNA, novel WT1 mRNA (2 kb), and cyclophilin mRNA (loading control). The analysis was conducted in three separated experiments. FIG. 3a shows the Northern blot hybridized with probe spanning 3'end of WT1 (exon 7–exon 10) (Table 1). The expected 3.1 kb transcript was detected only from PC-3. The novel short transcript was detected at 2 kb in P69SV40TAg and its sublines, but was absent from PC-3 cell. FIG. 3b shows the Northern blot hybridized with probe spanning 5' end of WT1 (exon 1–5) (Table 1) which reveals a strong hybridization signal only from PC-3 cells. Sample loading was normalized by comparison with stripped blot re-probed with riboprobe complementary to cyclophilin mRNA (template provided by Ambion, Inc.) as shown in FIG. 3c. The lanes in Figures a, b, and c are labeled as follows: M=>markers (kb) and the source of mRNA is identified by label at the top of each lane. Note: Figure c is at a higher magnification than Figures a and b.

RT-PCR spanning the 3' end of WT1 consistently detected WT1 transcripts in the P69SV40Tag and sublines, yet failed to detect the 5' end of WT1 mRNA when primers spanning the first five exons were used. Northern blot analysis of mRNA isolated from PC-3, P69SV49TAg, M2205, M2182, and M12 was performed. Filters containing these RNAs were hybridized with either a probe spanning portions of the 3' end, as shown in FIG. 3a, or the 5' end of WT1 as shown in FIG. 3b. With PC-3 mRNA, both the 3' probe and 5' probe hybridized with the expected 3.1 kb band as shown in FIG. 3a. As predicted by the RT-PCR results, an abnormally short transcript (approximately 2 kb) was detected in the P69SV40TAg and its sublines using the 3' WT1 probe as shown in FIG. 3a, indicated by the arrow. The 5' WT1 probes did not produce such a result. The shorter transcript was not observed in PC-3 mRNA. The blot was stripped, rehybridized with a cyclophilin probe and normalized for loading (FIG. 3c).

To further define the five prime end of the transcript, mRNA was isolated from M12 and analyzed by the 5' RACE procedure. Since both PCR and northern blot data supported the presence of all or part of exon 6 through exon 10 as being present in the short transcript, the final 3' PCR primer for the RACE procedure was placed in exon 6. The resulting PCR products were cloned and sequenced (FIGS. 4a and 4b).

FIGS. 4a and b shows the PCR product obtained from the 5' RACE procedure performed on mRNA from M12 cell was cloned and sequenced. Automated cycle squenced. Automated cycle sequencing by M13 forward primer (FIG. 4a) and M13 reverse primer (FIG. 4b) identified a portion of intron 5 sequence located at the 5' end of the transcript beginning 356 bp upstream from exon 6. The 101 bp portion of intron 5 from −101 to −1 was spliced out to generate the mature mRNA. The 5' RACE procedure was repeated twice and sequencing performed 3 times, with the same result. The sequence listing for the truncated region of the WT1 gene transcript shown in FIGS. 4a (SEQ ID NO: 34) and 4b (SEQ ID NO: 35) is shown in FIG. 4c (SEQ ID NO: 36). The sequence of the truncated WT1 5'-3' is shown starting from the 5'-most nucleotide detected by the 5' RACE procedure (−356 located in intron 5) and extending 3' to the nucleotide that occurs just before the beginning of exon 6 (nucleotide −102 located in intron 5; nucleotides −101 through −1 of intron 5 are not present in the truncated WT1 transcript).

This indicated that the 5' end of the abnormal sequence detected in M12 RNA included exon 6 and a portion of intron 5. The first nucleotide detected at the five prime end of the truncated WT1 transcript corresponded to nucleotide −356 relative to the first nucleotide in exon 6. However, nucleotides in intron 5 between −101 and −1 were missing from the transcript. These results are consistent with the belief that the elimination of nucleotides in intron 5 between −101 and −1 was through splicing using nucleotides −104 to −96 in intron 5 as a splice donor site and the normal nucleotides −3 to +1 of exon 6 as the splice acceptor site.

Western immunoblotting with anit-WT1 antibody C19, which recognizes the COOH terminus of WT1 protein, detected small proteins (23–31 kD) as immunodominant bands in P69, M12, and MCF7. K 562 cell expressed the expected 54 kD normal sized WT1 protein as well as the smaller proteins as shown in FIG. 5. The mRNA size and sequence data are approximately consistent with the size of protein detected. The 54, 24 and 31 kD proteins were not detected with C19 antibody preincubated with immunizing peptide.

FIG. 5 shows the expression of WT1 protein detected by western immunoblotting in human prostate cancer cell lines P69 and M12; breast cancer cell line, MCF7; and, leukemia cell line, K562. Total protein extracted as described in the example above was subjected to SDS-PAGE (10%), western blotted and exposed to antibody C19, which recognizes the COOH terminus of WT1. The immunodominant bands in P69, M12 and MCF7 migrated at 31 and 23 kD, but the expected 52–54 kD WT1 protein was absent. The positive control, K562, expressed the normal 54 kD protein as well as the shorter forms. These experiments were performed a minimum of 3 times. Migration of molecular weight marker indicated by number on left (kD). Source of protein indicated by names of cell lines at the top of the lanes.

This example demonstrates that the WT1 expression in PC-3 produces the expected normal site (3.1 kb) transcript, while the metastatic M12 subline of P69SV40TAg produces a novel shorter transcript (2 kb). Further, cloning and sequencing of the 2 kb transcript indicated the presence of exon 6 through 10 spliced to a portion of intron 5 at the 5' end of the truncated transcripts.

Figure 6:
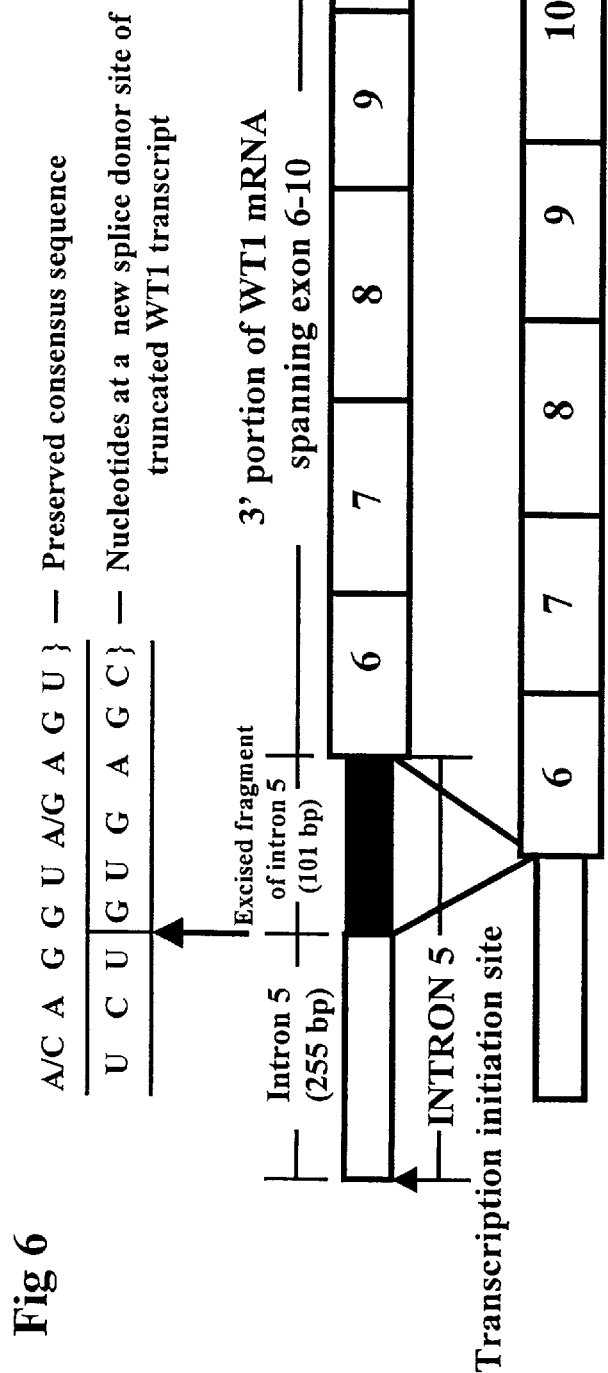
FIG. 6 shows a schematic diagram of possible origin of truncated WT1 and mRNA in human prostate cell lines where (A) shows pre-mRNA and (B) shows mature mRNA.

FIG. 6 shows a schematic diagram of possible origin of truncated WT1 mRNA in human prostate cell lines where (A) shows pre-mRNA and (B) shows mature mRNA. The 101 bp-portin of intron 5 is spliced out to make a mature mRNA, which consists of 3' portion of WT1 gene, is about 2000 bp in size, compatible with the size of transcripts detected by northern blot (FIG. 3a). The new splice donor site shows partially preserved consensus sequence.

As FIG. 1 illustrates, RT-PCR products of all cell lines prepared with primers spanning exons 8–10 hybridized with the 3' end probe. In contrast, the hybridization of the probe spanning the portion of the 5'end (FIG. 2) was not detected except in PC-3 cells.

A combination of northern blotting and 5' RACE allowed characterization of the 5' end. The P69SV40TAg cells and their sublines produced a 2 kb WT1 transcript (FIG. 3a), while the PC-3 cell produced the expected full length 3.1 kb WT1 transcript (FIG. 3b). When normalized for loading (FIG. 3c), the tumorigenic M2205 and M2182, and the metastatic M12 cells produced higher amounts of the short transcript than P69SV40TAg. Cloning and sequencing of the 2 kb transcript confirmed its identify with the 3' end of human WT1 (Gessler et al., 1990), and suggested a possible intronic start site within intron 5. Other human genes are known to exploit intronic promoters under appropriate conditions. The human mdm2 gene utilizes an intronic promoter that is p53-responsive. The c-kit gene uses a promoter in intron 16, which is active in a cell- and developmental-stage specific fashion. Without intending to bound by theory, the above observations are consistent with the possibility that the 2 kb transcript utilized a promoter located in intron 5. The existence of this shortened WT1 transcript, suggests a new mechanism of WT1 mediated oncogenesis.

EXAMPLE 2

The Truncated Wilms' Tumor Gene Transcript as a Marker for the Identification of Cancer To determine the feasibility of using the above findings as the basis for a new test for detecting neoplastic tissue, RT-PCR was performed using a 5prime primer located in intron 5 and a 3 prime primer located in exon 6 (Table 1).

Residual samples of prostate cancer tissue together with attached residual normal tissue were obtained from patients undergoing radical prostatectomy for treatment of their cancer. The tissue was frozen in liquid nitrogen immediately upon receipt by the pathology laboratory. Subsequently, the block of tissue was sectioned on a cryostat and the sections examined on a Pix Cell microdissector. Sections of tissue from areas of cancer were removed and RNA extracted essentially as described as above. From the same slide that contained the cancer, adjacent normal tissue was identified morphologically and similarly removed from the slide and subjected to the RNA extraction procedure as described above. At the conclusion of the extraction procedure glycogen was added as carrier at a final concentration of approximately 0.1 $\mu g/\mu l$ and the RNA was precipitated with an equal volume of isopropanol. The resulting precipitate was dissolved in 20 $\mu l$ of 1 x SSC containing 1 U/$\mu l$ of Rnasin and 3.5 $\mu l$ aliquots were used in an RT reaction totaling 12.0 $\mu l$ as described in the preceding sectin on RT-PCR.

FIG. 7 shows the RT-PCR product using primers in intron 5 and exon 6. Total RNA was obtained from microdissected frozen normal (N) and primary prostate cancer (T) tissue from two patients and from M12, PC3 and K562 cell lines. The products from RT-PCR were examined on 1.5% agarose gel, transferred to nylon membrane and probed with an oligonucleotide in exon 6 (Table 1; #11; sense oligonucleotide). The 196 bp fragment present in all samples represents an amplified product from contaminating DNA. The 95 bp fragment represents a product from the truncated transcript in which a 101 bp segment of intron 5 between −101 and −1 has been removed by splicing.

FIG. 7 shows the results of a study comparing RNA from microdissected frozen normal (N) and primary prostate cancer (T) tissue from two patients and from M12, PC3 and K562 cell lines. The 95 bp fragment representing the product from the truncated transcript was seen in one of the two primary cancers and in the M12 and K562 cell lines, but not in the two normal tissue samples. In addition, total RNA from normal peripheral blood lymphocytes likewise showed no 95 bp product while the 95 bp product was present in RNA from two cases of primary acute leukemia. Thus, based on the examined tissues, the absence of the 101 bp segment of intron 5 between −101 and −1 is a method for distinguishing the presence of the truncated transcript from contaminating normal WT1 sequence and has only been observed in neoplastic primary tumor tissue or tumorigenic cell lines.

It will therefore be readily understood by those persons skilled in the art that the present invention is susceptible to broad utility and application. Many embodiments and adaptations of the present invention other than those herein described, as well as many variations, modifications and equivalent arrangement, will be apparent from or reasonably suggested by the present invention and the foregoing description thereof, without departing from the substance or scope of the present invention.

Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims and the equivalents thereof.

TABLE 1

Primers and Probes

| No. | Function | Sense Primer or Probe | Antisense | Position | Size bp |
|---|---|---|---|---|---|
| 1 | RT-PCR exon 1–2 | 5'-TGA GCG CCT TCA CTG TCC AC-3' (SEQ ID NO: 7) | 5'-GAA GGT GAC CGT GCT GTA AC-3' (SEQ ID NO: 24) | 646–842 | 197 |
| 2 | Probe in exon 1 | 5'CCG GCT GTG CCA GTG AAC-3' (SEQ ID NO: 8) | | 695 | |
| 3 | RT-PCR exon 2–3 | 5'-CCA ACC ACT CAT TCA AGC-3' (SEQ ID NO: 9) | 5'-GGT GTG GCA GCC ATA GAC C-3' (SEQ ID NO: 25) | 895–992 | 98 |
| 4 | Probe in exon 3 | 5'-GTG AGC AGC AGT ACT CGG TG-3' (SEQ ID NO: 10) | | 946 | |
| 5 | RT-PCR exon 3–4 | 5'-GTG AGC AGC AGT ACT CGG TG-3' (SEQ ID NO: 11) | 5'-GGT GGC TCC TAA GTT CAT CT-3' (SEQ ID NO: 26) | 946–1118 | 173 |
| 6 | Probe in exon 3 | 5' GGT GTG GCA GCC ATA GAC C-3' (SEQ ID NO: 12) | | 992 | |
| 7 | RT-PCR exon 4–5 | 5'-CCA GCT TGA ATG CAT GAC-3' (SEQ ID NO: 13) | 5'-TGC TCT GCC CTT CTG TC-3' (SEQ ID NO: 27) | 1073–1176 | 104 |
| 8 | probe in exon 5 | 5'-AGC TCC AGC TCA GTG AAA TG-3' (SEQ ID NO: 14) | | 1140 | |
| 9 | RT-PCR exon 5–6 | 5'-AGC TCC AGC TCA GTG AAA TG-3' (SEQ ID NO: 15) | 5'-CAC CGT GCG TGT GTA TTC-3' (SEQ ID NO: 28) | 1140–1257 | 118 |
| 10 | probe in exon 5 | 5'-TGC TCT GCC CTT CTG TC-3' (SEQ ID NO: 16) | | 1176 | |
| 11 | RT-PCR exon 6–7 | 5'-CCA CAG CAC AGG GTA CGA-3' (SEQ ID NO: 17) | 5'-CTG CTG TGC ATC TGT AAG TG-3' (SEQ ID NO: 29) | 1178–1414 | 237 |
| 12 | probe in exon 6 | 5'-GAA TAC ACA CGC ACG GTG-3' (SEQ ID NO: 18) | | 1257 | |
| 13 | RT-PCR exon 8–10 | 5'-AGA CAT ACA GGT GTG AAA CC-3' (SEQ ID NO: 19) | 5'-TCA AAG CGC CAG CTG GAG TTT-3' (SEQ ID NO: 30) | 1506–1730 | 225 |
| 14 | Probe in exon 10 | 5'-CGG TGG CCA AGT TGT CAG AA-3' (SEQ ID NO: 20) | | 1648 | |
| 15 | RT-PCR exon 1–5 (For riboprobe) | 5'-CCG CCT CAC TCC TTC ATC AA-3' (SEQ ID NO: 21) | 5'-CAT TTC ACT GAG CTG GAG CT-3' (SEQ ID NO: 31) | 579–1159 | 581 |
| 16 | RT-PCR exon 7–10 (For riboprobe) | 5'-GCT GTC CCA CTT ACA GAT GCA-3' (SEQ ID NO: 22) | 5'-GAG AGT CAG ACT TGA AAG CAG-3' (SEQ ID NO: 32) | 1388–1801 | 414 |
| 17 | RT-PCR intron 5–exon 6 | 5'-GAA CCC TGC ATC TAA AGT GG-3' (SEQ ID NO: 23) | 5'-CGT TGT GTG GTT ATC GCT CT-3' (SEQ ID NO: 33) | −159*–1195 | 196−= |

Note. Numbering of the corresponding cDNA sequence refers the published sequence (Gessler et al., 1990).

What is claimed is:

1. A method for detecting cancer in a subject, the method comprising:
   obtaining a sample from the subject; and
   detecting a truncated WT1 gene transcript in the sample, wherein the truncated WT1 gene transcript comprises RNA complementary to a portion of intron 5 linked to RNA complementary to exons 6–10 and lacks RNA complementary to exons 1–5, and wherein the presence of the truncated WT1 gene transcript indicates the presence of cancer.

2. The method of claim 1 wherein the truncated WT1 gene transcript lacks RNA complementary to a 101 base pair segment of intron 5 between positions −101 and −1.

3. The method of claim 1 wherein the truncated gene transcript includes RNA complementary to SEQ ID NO: 36.

4. The method of claim 1 wherein the detection of the truncated WT1 gene transcript further includes performing reverse transcriptase-polymerase chain reaction using a 5' primer wherein said 5' primer specifically hybridizes to sequences in intron 5 and a 3' primer wherein said 3' primer specifically hybridizes to sequences in exon 6.

5. The method of claim 4 wherein the 5' primer is 5'-GAA CCC TGC ATC TAA AGT GG-3' (SEQ ID NO: 1).

6. The method of claim 4 wherein the detection of the truncated WT1 gene transcript further includes probing cDNA products from the reverse transcriptase-polymerase chain reaction with an oligonucleotide probe wherein the oligonucleotide probe specifically hybridizes to sequences in exon 6.

7. The method of claim 6 wherein detection of the truncated WT1 gene transcript further includes identifying a 95 base pair cDNA product.

8. The method of claim 1 wherein the truncated gene transcript has a length of about two thousand nucleotides.

9. The method of claim 1 wherein positive detection indicates the presence of prostate cancer.

10. The method of claim 1 wherein positive detection indicates the presence of breast cancer.

11. The method of claim 1 wherein positive detection indicates the presence of leukemia.

12. A method for detecting a truncated WT1 gene transcript, the method comprising, obtaining a nucleic acid sample from a subject suitable for performing reverse transcriptase-polymerase chain reaction;

performing reverse transcriptase-polymerase chain reaction on the nucleic acid sample using a 5' primer that specifically hybridizes to sequences in intron 5 and a 3' primer that specifically hybridizes to sequences in exon 6, wherein the step of performing generates cDNA fragments which are reverse transcriptase-polymerase chain reaction products;

probing the cDNA fragments with a labeled oligonucleotide probe that specifically hybridizes to sequences in exon 6, creating labeled cDNA/probe hybrids; and identifying the labeled cDNA/probe hybrids, wherein identification of the labeled cDNA/probe hybrids is indicative of the presence of the truncated WT1 gene transcript in the sample.

13. The method of claim 12 wherein the oligonucleotide probe is 5'-CCA CAG CAC AGG GTA CGA-3' (SEQ ID NO: 2).

14. The method of claim 12 wherein the 5' primer used for performing reverse transcriptase-polymerase chain reaction is 5'-GAA CCC TGC ATC TAA AGT GG-3' (SEQ ID NO: 1).

15. The method of claim 12 wherein the truncated gene transcript includes RNA complementary to SEQ ID NO: 36.

16. The method of claim 12 wherein the cDNA fragments are 95 base pair fragments.

17. The method of claim 1 wherein said portion of intron 5 comprises nucleotides from position −255 to position −102.

18. The method of claim 6 wherein the oligonucleotide probe is 5'-CCA CAG CAC AGG GTA CGA-3' (SEQ ID NO: 2).

* * * * *

SEQUENCE LISTING

<160> NUMBER OF SEQ ID NOS: 36

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 1
gaaccctgca tctaaagtgg                                                    20

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 2
ccacagcaca gggtacga                                                      18

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 3
accttcgttc acagtccttg                                                    20

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 4
ctgctgtgca tctgtaagtg ggacagc                                            27

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 5
cgttgtgtgg ttatcgctct                                                    20

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 6
ctcgtaccct gtgctgtgg                                                     19

<210> SEQ ID NO 7
<211> LENGTH: 20

```
<212> TYPE: DNA
<213> ORGANISM: Artificial Sequence
<220> FEATURE:
<223> OTHER INFORMATION: Description of Artificial Sequence: Primer

<400> SEQUENCE: 7
tgagcgcctt cactgtccac                                                   20

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Probe

<400> SEQUENCE: 8
ccggctgtgc cagtgaac                                                     18

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 9
ccaaccactc attcaagc                                                     18

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Probe

<400> SEQUENCE: 10
gtgagcagca gtactcggtg                                                   20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 11
gtgagcagca gtactcggtg                                                   20

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Probe

<400> SEQUENCE: 12
ggtgtggcag ccatagacc                                                    19

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 13
```

```
ccagcttgaa tgcatgac                                                 18

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Probe

<400> SEQUENCE: 14
agctccagct cagtgaaatg                                               20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 15
agctccagct cagtgaaatg                                               20

<210> SEQ ID NO 16
<211> LENGTH: 17
<212> TYPE: DNA
<213> ORGANISM: Artificial Sequence
<220> FEATURE:
<223> OTHER INFORMATION: Description of Artificial Sequence: Probe

<400> SEQUENCE: 16
tgctctgccc ttctgtc                                                  17

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 17
ccacagcaca gggtacga                                                 18

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Probe

<400> SEQUENCE: 18
gaatacacac gcacggtg                                                 18

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 19
agacatacag gtgtgaaacc                                               20

<210> SEQ ID NO 20
<211> LENGTH: 20
<212> TYPE: DNA
<213> ORGANISM: Artificial Sequence
```

```
<220> FEATURE:
<223> OTHER INFORMATION: Description of Artificial Sequence: Probe

<400> SEQUENCE: 20
cggtggccaa gttgtcagaa                                                    20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 21
ccgcctcact ccttcatcaa                                                    20

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 22
gctgtcccac ttacagatgc a                                                  21

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 23
gaaccctgca tctaaagtgg                                                    20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 24
gaaggtgacc gtgctgtaac                                                    20

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 25
ggtgtggcag ccatagacc                                                     19

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 26
ggtggctcct aagttcatct                                                    20
```

```
<210> SEQ ID NO 27
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 27
tgctctgccc ttctgtc                                                  17

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 28
caccgtgcgt gtgtattc                                                 18

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 29
ctgctgtgca tctgtaagtg                                               20

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 30
tcaaagcgcc agctggagtt t                                             21

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 31
catttcactg agctggagct                                               20

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 32
gagagtcaga cttgaaagca g                                             21

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Primer
```

-continued

<400> SEQUENCE: 33
cgttgtgtgg ttatcgctct                                                        20

<210> SEQ ID NO 34
<211> LENGTH: 193
<212> TYPE: DNA
<213> ORGANISM: Homo sapiens
<220> FEATURE:
<223> OTHER INFORMATION: Wilms Tumor 1 (WT1)

<400> SEQUENCE: 34
cgactagtac ggggggggg gcggtgggat tcctgagata cctgcagctg tcagccctgc             60
cgtctagatg gtaaacaact tgccgaggat gaaaccctgc cactgtggtc ttcctcggct            120
tgtctgagcg agacctagac cgtgacggtg cacgcctacg agaatcggag gatgagggag            180
gggctgcgag gtg                                                               193

<210> SEQ ID NO 35
<211> LENGTH: 198
<212> TYPE: DNA
<213> ORGANISM: Homo sapiens
<220> FEATURE:
<223> OTHER INFORMATION: Wilms Tumor 1 (WT1)

<400> SEQUENCE: 35
caaaagctgg agctccaccg cggtggcggc cgctctagcc ccgttgtgtg gttatcgctc            60
tcgtaccctg tgctgtggag aacaaaaata gttggttttt gcctccctcc atggggccac           120
tttagatgca gggttctgcg gagggcgagg ccctggatc ctggccgcca cctcgcagcc            180
cctccctcat cctccgat                                                          198

<210> SEQ ID NO 36
<211> LENGTH: 255
<212> TYPE: DNA
<213> ORGANISM: Homo sapiens
<220> FEATURE:
<223> OTHER INFORMATION: Wilms Tumor 1 (WT1)

<400> SEQUENCE: 36
attcctgaga tacctgcagc tgtcagccct gccgtctaga tggtaaacaa cttgccgagg            60
atgaaaccct gccactgtgg tcttcctcgg cttgtctgag cgagacctag accgtgacgg           120
tgcacgccta cgagaatcgg aggatgaggg aggggctgcg aggtggcggc caggatccag           180
gggcctcgcc ctccgcagaa ccctgcatct aaagtggccc catggaggga ggcaaaaacc           240
aactattttt gttct                                                             255